US009044378B2

(12) United States Patent
Verespej et al.

(10) Patent No.: US 9,044,378 B2
(45) Date of Patent: Jun. 2, 2015

(54) ANTI-NEEDLE STICK SAFETY DEVICE OR SYSTEM FOR USE WITH DRUGS REQUIRING RECONSTITUTION

(75) Inventors: James M. Verespej, San Marcos, CA (US); Lars T. Westbye, Carlsbad, CA (US); Philip Dowds, San Diego, CA (US)

(73) Assignee: SAFETY SYRINGES, INC., Carlsbad, CA (US)

( * ) Notice: Subject to any disclaimer, the term of this patent is extended or adjusted under 35 U.S.C. 154(b) by 688 days.

(21) Appl. No.: 12/129,459

(22) Filed: May 29, 2008

(65) Prior Publication Data

US 2008/0300549 A1 Dec. 4, 2008

Related U.S. Application Data

(60) Provisional application No. 60/941,209, filed on May 31, 2007.

(51) Int. Cl.
*A61M 5/32* (2006.01)
*A61M 5/00* (2006.01)
*A61M 5/178* (2006.01)
*A61J 1/20* (2006.01)
*A61M 5/31* (2006.01)

(52) U.S. Cl.
CPC .......... *A61J 1/2096* (2013.01); *A61J 2001/201* (2013.01); *A61J 2001/2055* (2013.01); *A61M 5/1782* (2013.01); *A61M 5/326* (2013.01); *A61M 2005/3114* (2013.01); *A61M 2005/3247* (2013.01); *A61M 2005/3261* (2013.01); *A61M 2005/3264* (2013.01)

(58) Field of Classification Search
CPC ............ A61M 5/3271; A61M 5/1782; A61M 5/3202; A61J 1/2096; A61J 2001/201
USPC ............ 604/110, 111, 164.08, 187, 192, 197, 604/198
See application file for complete search history.

(56) References Cited

U.S. PATENT DOCUMENTS

| 3,548,824 A | 12/1970 | Carr |
| 4,060,082 A | 11/1977 | Lindberg et al. |
| 5,201,708 A | 4/1993 | Martin |

(Continued)

FOREIGN PATENT DOCUMENTS

| FR | 2861310 A | 4/2005 |
| GB | 2079607 A | 1/1982 |

(Continued)

OTHER PUBLICATIONS

Instructions for Use for Bio-Set Injection from Bio-Set Website, printed Jan. 14, 2003 (http://www.bio-set.com/htm/InstUseInj.htm).

(Continued)

*Primary Examiner* — Theodore Stigell
*Assistant Examiner* — Lauren M Peng
(74) *Attorney, Agent, or Firm* — One LLP

(57) ABSTRACT

The present disclosure describes a needle guard device or system that can be used with drugs requiring reconstitution. The needle guard is preferably a passive needle guard that can be used during reconstitution without activating the safety mechanism. Following administration of the medication, the needle guard shields a user from inadvertent needle sticks by extending a protective shield over the needle.

16 Claims, 10 Drawing Sheets

(56) References Cited

U.S. PATENT DOCUMENTS

| | | | |
|---|---|---|---|
| 5,279,583 A | 1/1994 | Shober, Jr. | |
| 5,320,603 A | 6/1994 | Vetter et al. | |
| 5,324,265 A | 6/1994 | Murray | |
| 5,389,085 A | 2/1995 | D'Alessio | |
| 5,569,193 A | 10/1996 | Hofstetter et al. | |
| 5,591,138 A | 1/1997 | Vaillancourt | |
| 5,779,668 A | 7/1998 | Grabenkort | |
| 5,785,682 A | 7/1998 | Grabenkort | |
| 5,971,953 A | 10/1999 | Bachynsky | |
| 5,976,111 A | 11/1999 | Hart | |
| 6,149,623 A | 11/2000 | Reynolds | |
| 6,149,629 A * | 11/2000 | Wilson et al. | 604/198 |
| 6,186,980 B1 | 2/2001 | Brunel | |
| 6,253,804 B1 | 7/2001 | Safabash | |
| 6,364,865 B1 | 4/2002 | Lavi et al. | |
| 6,379,336 B1 | 4/2002 | Asbaghi | |
| 6,440,101 B1 | 8/2002 | Grabenkort et al. | |
| 6,474,369 B2 | 11/2002 | Castellano | |
| 6,478,771 B1 | 11/2002 | Lavi et al. | |
| 6,623,459 B1 | 9/2003 | Doyle | |
| 6,656,163 B1 * | 12/2003 | Marshall et al. | 604/198 |
| 6,729,370 B2 | 5/2004 | Norton | |
| 6,869,415 B2 | 3/2005 | Asbaghi | |
| 6,939,330 B1 * | 9/2005 | McConnell-Montalvo et al. | 604/197 |
| 7,140,401 B2 | 11/2006 | Wilcox | |
| 7,207,973 B2 | 4/2007 | Barrella | |
| 7,294,119 B2 | 11/2007 | Westbye | |
| 7,314,464 B2 | 1/2008 | Giambattista | |
| 2003/0105430 A1 * | 6/2003 | Lavi et al. | 604/136 |
| 2005/0277894 A1 * | 12/2005 | Westbye et al. | 604/198 |
| 2006/0089594 A1 * | 4/2006 | Landau | 604/68 |
| 2006/0111679 A1 | 5/2006 | Millerd | |
| 2007/0179441 A1 * | 8/2007 | Chevallier | 604/110 |
| 2007/0265576 A1 * | 11/2007 | Pessin | 604/198 |
| 2008/0015513 A1 | 1/2008 | Westbye et al. | |

FOREIGN PATENT DOCUMENTS

| | | |
|---|---|---|
| WO | WO 95/31235 A | 11/1995 |
| WO | WO 01/45776 A | 6/2001 |
| WO | WO 02/072182 A | 9/2002 |
| WO | WO 02/076542 A | 10/2002 |
| WO | WO 2004/045685 A | 6/2004 |

OTHER PUBLICATIONS

Press Release from PRWeb Website entitled "Second Patent for Mixing Lyophilized (Freeze-Dried) Drugs in a Needle-Less Injector Awarded to Penject® Corporation," printed Jan. 14, 2003 (http://www.prweb.com/printer.php?prid=31822).

Pre-Filled Diluent and Pre-filled Drug Syringes (http://www.baxterdrugdelivery.com/deliverysystems/syringes.html) Jan. 4, 2003 (2 pages).

* cited by examiner

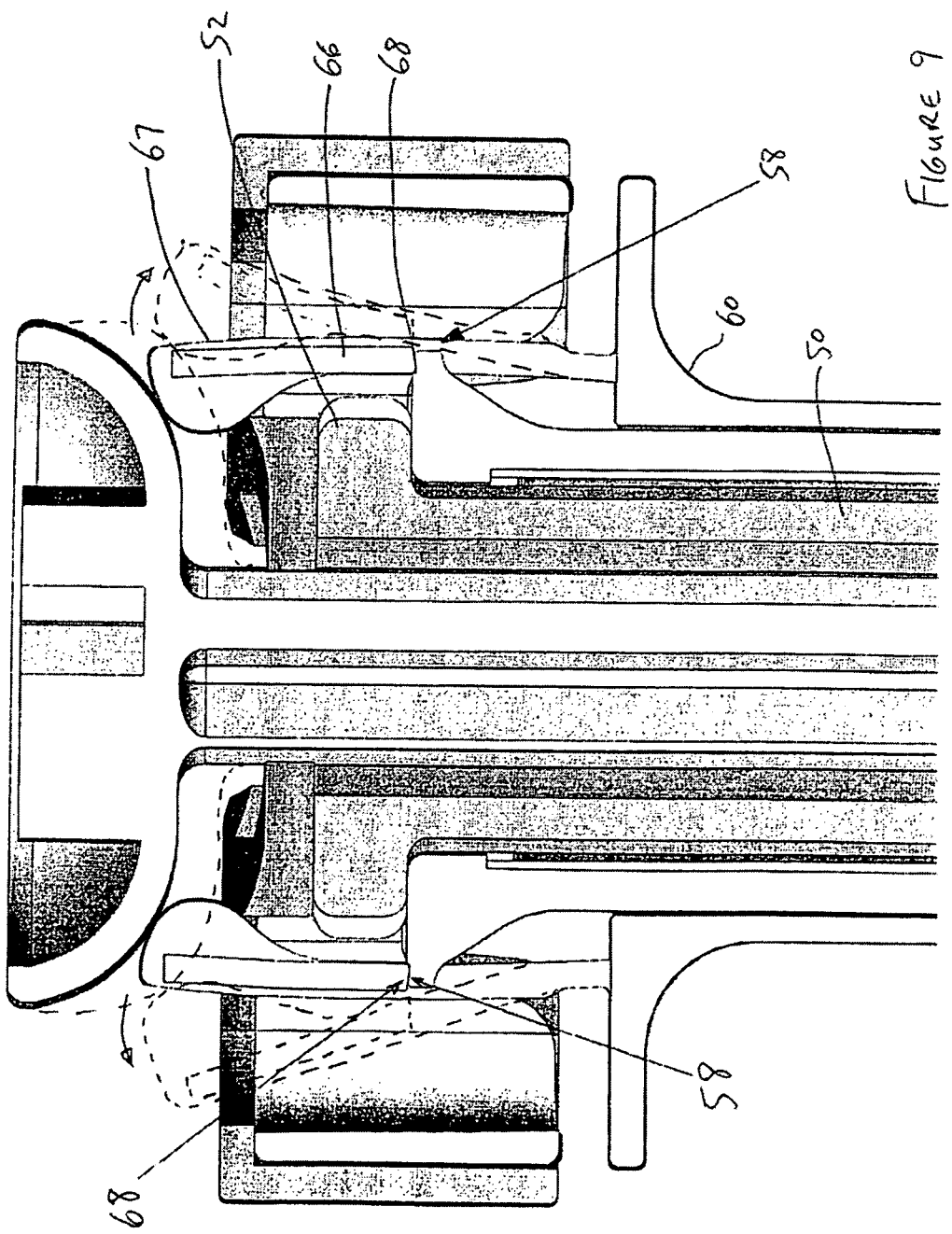

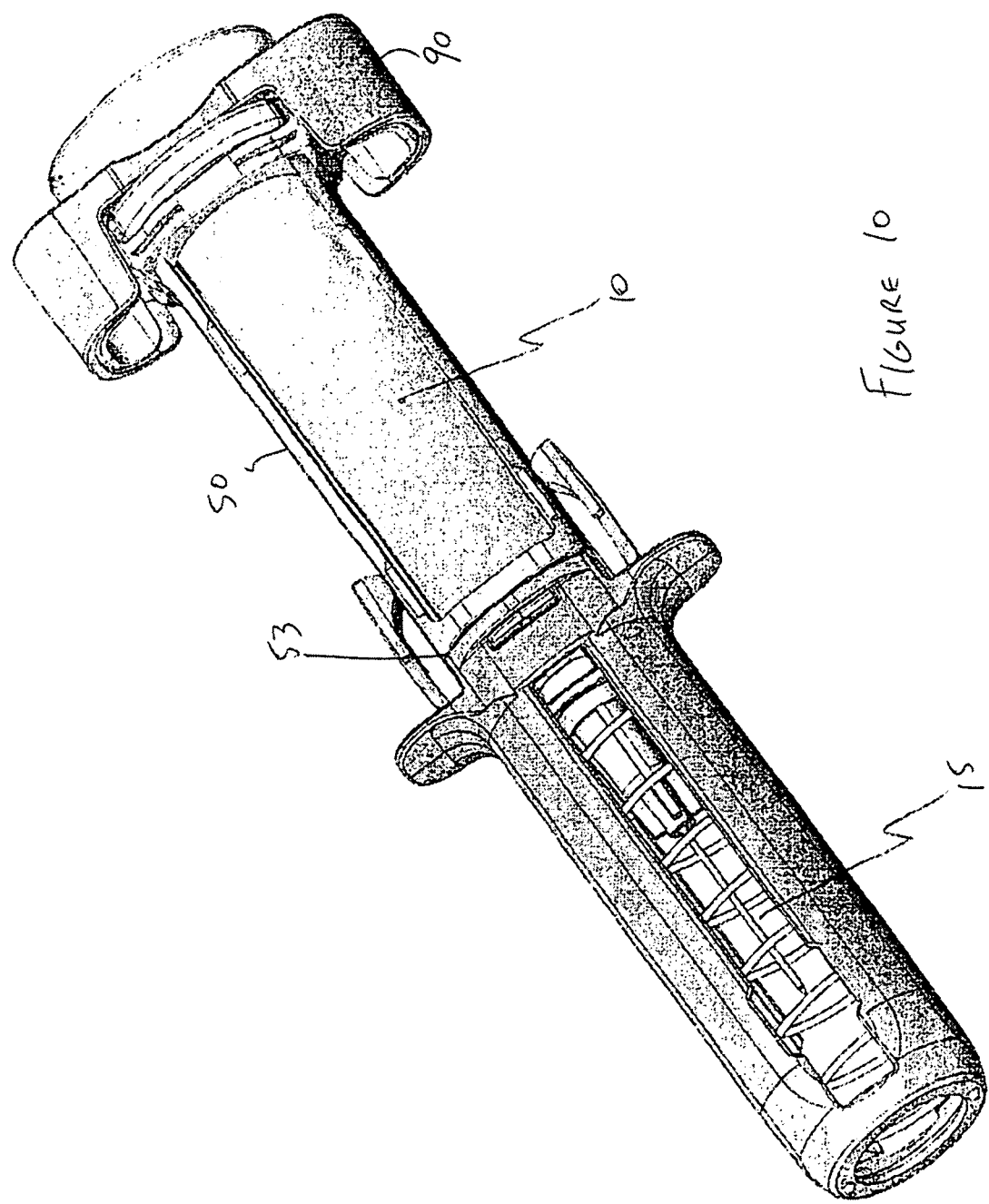

ANTI-NEEDLE STICK SAFETY DEVICE OR SYSTEM FOR USE WITH DRUGS REQUIRING RECONSTITUTION

CROSS-RELATIONSHIP TO PENDING APPLICATION

This application claims priority to provisional application Ser. No. 60/941,209 filed May 31, 2007, and is incorporated herein by reference.

FIELD

This invention relates generally to syringe systems and methods for mixing and delivering a therapeutic agent formed by combining a diluent with a lyophilized drug or a concentrated drug. More specifically, this invention relates to syringe systems, including a passive needle guard, used for reconstitution of lyophilized or concentrated drugs and methods for using such systems.

BACKGROUND

Lyophilization is a process by which the volatile components of a drug are removed in order to extend the shelf-life of the medication. Lyophilization may involve the rapid freezing of a material at a very low temperature followed by rapid dehydration. Solvents such as water are removed from the drug yielding a substance that is more stable and can be stored. Lyophilized drugs are generally stored in a glass vial or cartridge and covered by a rubber stopper or septum.

In order to administer the lyophilized drugs, the drug must generally be reconstituted. Reconstitution is the process of hydrating drugs that are packaged and stored in a dry lyophilized state. A diluent, such as water, saline, 5% Aqueous Dextrose or the like, is added to the lyophilized drug and the combination is mixed until the drug is fully dissolved. A syringe is typically used to inject the diluent into the vial containing the lyophilized drug. The syringe may be pre-filled with the diluent or the user may first withdraw the diluent from a second vial or container into the syringe. After the diluent is added to the vial containing the lyophilized drugs, the contents are then mixed to form a therapeutic agent.

After complete mixing of the diluent and the lyophilized drug, the therapeutic agent may be aspirated back into the syringe. Once the therapeutic agent is in the syringe, the medication is administered to the patient. Usually the therapeutic agent is administered within a short time after reconstitution in order to ensure that the drug is not degraded by the solvent.

Most current systems for reconstitution expose the user to the risk of inadvertent needle sticks. In addition, current systems may not adequately prevent the possible reuse of the syringe. A number of needle guards for syringes have been developed that are intended to prevent accidental needle sticks and/or inadvertent reuse of a syringe. However, because syringe safety shield devices normally actuate when the plunger is fully advanced during the administration of the drug, these same devices will prematurely actuate the safety shield during the drug reconstitution phase as the diluent is added to the lyophilized drug. Therefore, a method for preventing the activation of the safety shield during drug reconstitution is highly desirable.

Accordingly, a syringe system that can be used for reconstitution and that would automatically activate a needle shield during or following administration of the therapeutic agent would be considered useful.

SUMMARY

The present invention is directed to a syringe system for reconstitution of lyophilized or concentrated drugs. The present invention is also directed to the combination of such a system with a passive needle guard that is automatically activated to extend a shield to cover a needle of the syringe and to methods of making and using such systems. Typically, a passive needle guard shield is activated when a radial portion or thumb pad of a plunger contacts a lateral catch or trigger finger of the passive needle guard. As the thumb pad of the plunger is moved distally, the trigger finger is forced laterally which results in a shield being forced distally to cover a needle of the syringe or in some designs, the syringe needle withdraws into the shield.

The present disclosure describes a needle guard device or system that can be used with drugs requiring reconstitution without activating the safety mechanism, yet provides needle safety shielding after the drug has been injected into the patient. In a preferred embodiment, the needle guard device would be assembled and sold with a syringe that is preferably pre-filled with the diluent.

DESCRIPTION OF THE DRAWINGS

FIG. 9 shows a profile sectional view of the diagram in FIG. 8. The dotted outline of the shield trigger fingers are shown in the unlatched position. The unlatched position is created when the plunger advances distally to an extent that the curved undersurface of the thumb pad pushes against the trigger fingers and displaces them laterally such that the latch surfaces of the shield trigger fingers and body are no longer engaged and will allow the shield to move distally with respect to the body.

FIG. 10 shows an exemplary embodiment of the device with the shield in the extended position.

DETAILED DESCRIPTION

Figure 1:
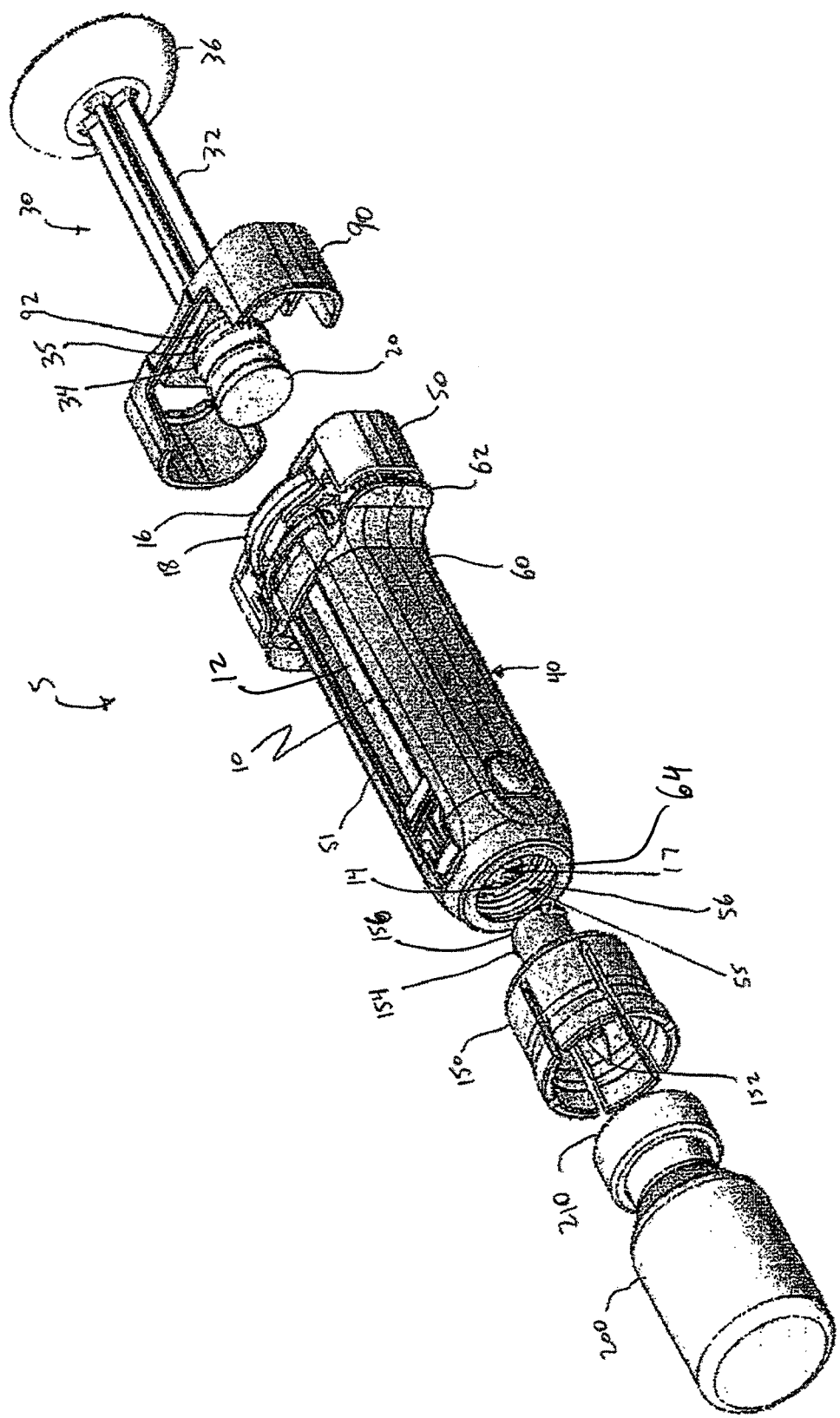
FIG. 1 shows an unassembled version of an exemplary embodiment of the device depicting the drug vial, drug vial adaptor, back plate, plunger, and the needle guard with an installed syringe.

Turning to the figures, FIG. 1 depicts an exemplary embodiment of the present needle safety guard device 5 and related components in an unassembled arrangement. As will be discussed in greater detail herein, FIG. 1 shows a drug vial 200, vial adaptor 150, needle guard 40 housing a syringe 10, back plate 90, stopper 20, and plunger 30. In FIG. 1, the plunger 30, stopper 20, and supporting back plate 90 are shown separated from the rest of the safety device to better illustrate the components, however, in a preferred embodiment they are connected to the main part of the safety device 5 as shown in FIG. 2.

In accordance with one aspect of the present disclosure, a medicine cartridge, such as a syringe 10 is provided (FIG. 1). Preferably, the syringe 10 has a substantially smooth-walled cylindrical barrel 12, a hub or distal end 14 that is the administration end, and a proximal end 16 having a flange 18. The cylindrical barrel 12 typically is manufactured from substantially clear glass. Alternatively, the barrel 12 may be manufactured from plastic, e.g., polypropylene, k-resin, or polycarbonate, and the like.

The barrel 12 of the syringe 10 may be pre-filled with a diluent, or may be filled with the diluent at a later step. Preferably the syringe 10, if pre-filled, also comprises a label or markings that indicates the quantity and type of diluent. For example, a sticker or label may be attached to the barrel 12 of the syringe 10 which provides the name of the diluent and the volume of the diluent. The diluent may be of any type known in the art including, but not limited to, sterile water, saline, 5% Aqueous Dextrose or the like. Alternatively, the user may aspirate the diluent into the syringe from a vial or container.

Figure 2:
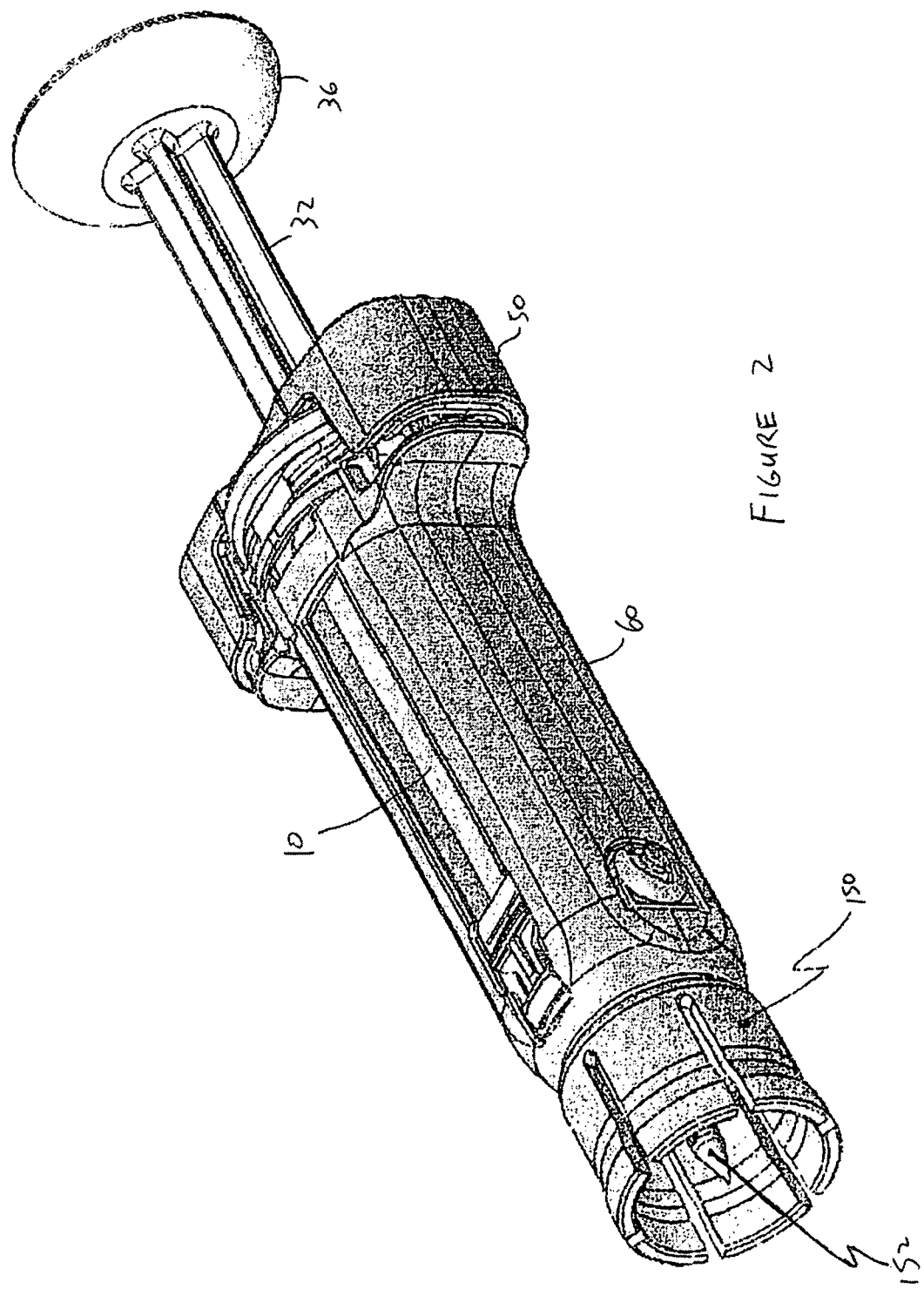
FIG. 2 shows an exemplary embodiment wherein the drug vial adaptor is removably coupled with the needle guard and syringe via luer fittings.

The proximal end 16 of the barrel 12 is configured to receive a stopper 20 and a plunger 30 (FIGS. 1 and 2). The stopper 20 is configured to be slidably coupled into the cylindrical barrel 12 and movable from a proximal position to a distal position (FIG. 1). The stopper 20 is preferably made of pliable rubber, thermoplastic rubber, plastic or similar material. The plunger 30 comprises a stem 32, a distal end 34, and a radial portion or thumb pad 36. The plunger 30 is generally made of plastic, e.g. polypropylene, k-resin, or polycarbonate, or the like.

The distal end 14 of the cylindrical barrel 12 comprises a needle port or luer fitting 17 (FIG. 1). The luer fitting 17 may be configured to couple with several different sizes of needles with different diameters and lengths or with other components that include a luer fitting or other type of holder. The needles and components may be connected by a Luer connector, Luer slip, Luer, or other holder as is known in the art. The luer fitting can be either of the slip version (no threads) or include threads. The luer fitting 17 is configured to allow interchanging of the needle and/or components so a user may use the most appropriate needle or component during filling the syringe, reconstitution, and administration of the medication to a patient.

The syringe 10 is housed inside the needle guard 40 wherein the needle guard 40 is preferably a passive needle guard (FIG. 1). Safety shield devices generally function, by covering the needle with a rigid cylindrical shield that surrounds the needle and projects far enough beyond the distal tip of the needle so as to prevent a user's finger from coming in contact with the needle tip. To prevent a user from forgetting to deploy the safety shield, preferred safety devices operate passively or automatically by providing a mechanism that initiates and physically executes the shielding of the needle after the injection has been completed. The passive needle guard 40 generally comprises a body 50 for receiving and holding the syringe 10, a shield 60 slidably attached to the body 50, and a spring mechanism 55 (FIG. 10). Both the body 50 and the shield 60 are generally molded from plastic, such as, polypropylene, k-resin, or polycarbonate, or the like. In a preferred embodiment, the body 50 and the shield 60 are substantially clear to facilitate observation of the syringe 10 therein. Alternatively, the body 50 and the shield 60 may be translucent or opaque, and may be colored, such as a latex color, a flesh tone, or a primary color.

Figure 6:
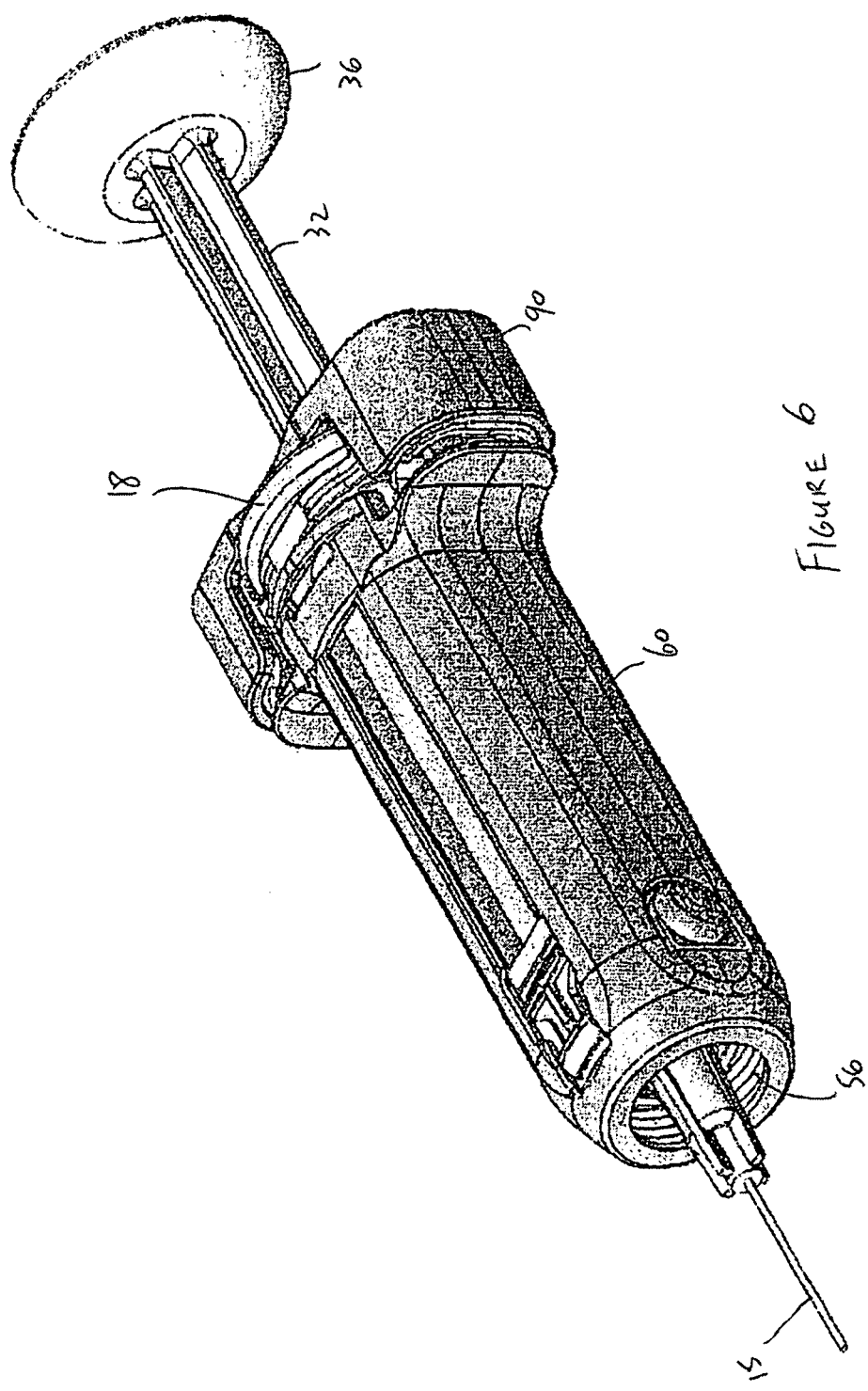
FIG. 6 shows an exemplary embodiment of the device after the reconstituted drug has been pulled into the syringe as shown in FIG. 5 and the drug vial adaptor has been replaced with an injection needle.

The body 50 may comprise opposing side rails defining two elongate openings or windows 51 extending at least partially between a proximal end 52 and a distal end 53 of the body 50 (FIGS. 1, 9, and 10). A substantially rigid collar is molded on the distal end 53 of the body 50. The collar preferably has a substantially annular shape. The collar defines an opening 56 for allowing a needle 15 on a syringe 10 received in the opening 56 to extend distally beyond the body 50 (FIGS. 1 and 6).

Figure 7:
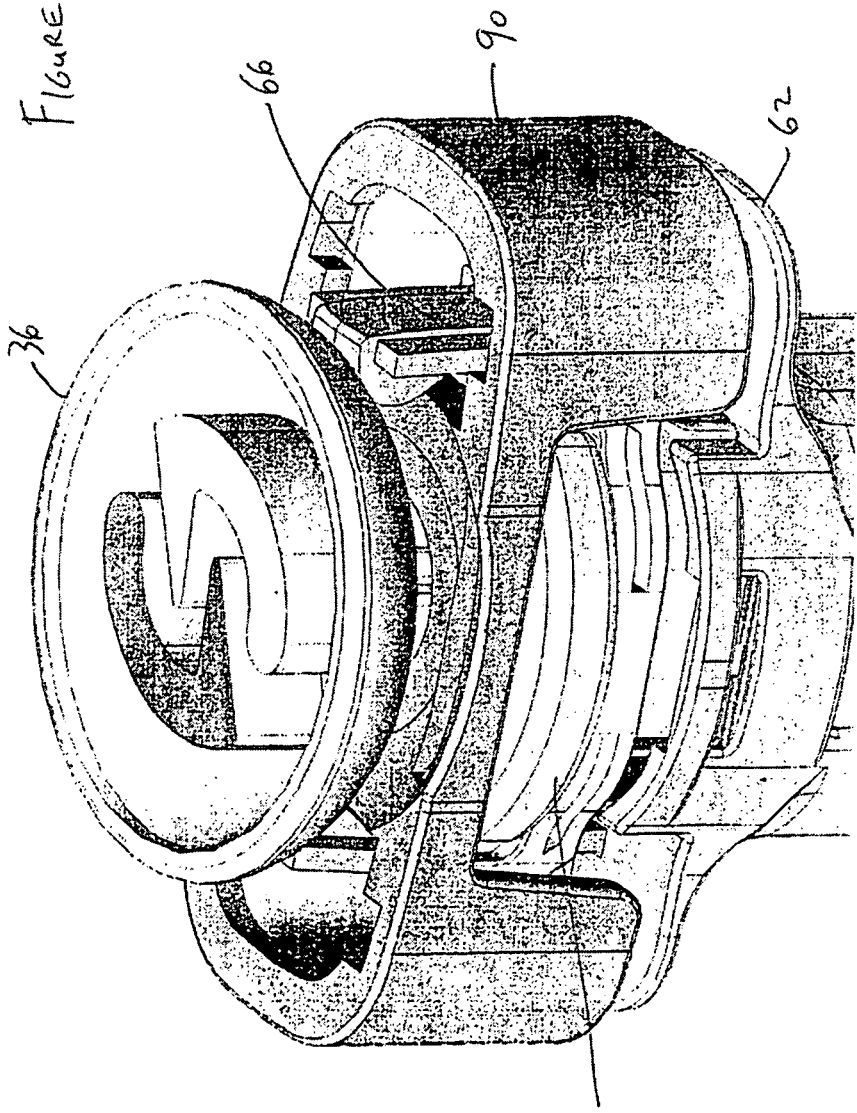
FIG. 7 shows an exemplary embodiment of the device showing the latched position of the shield trigger fingers. The curved under surface of the thumb pad of the plunger is in approximate contact with the proximal end of the trigger fingers.
Figure 8:
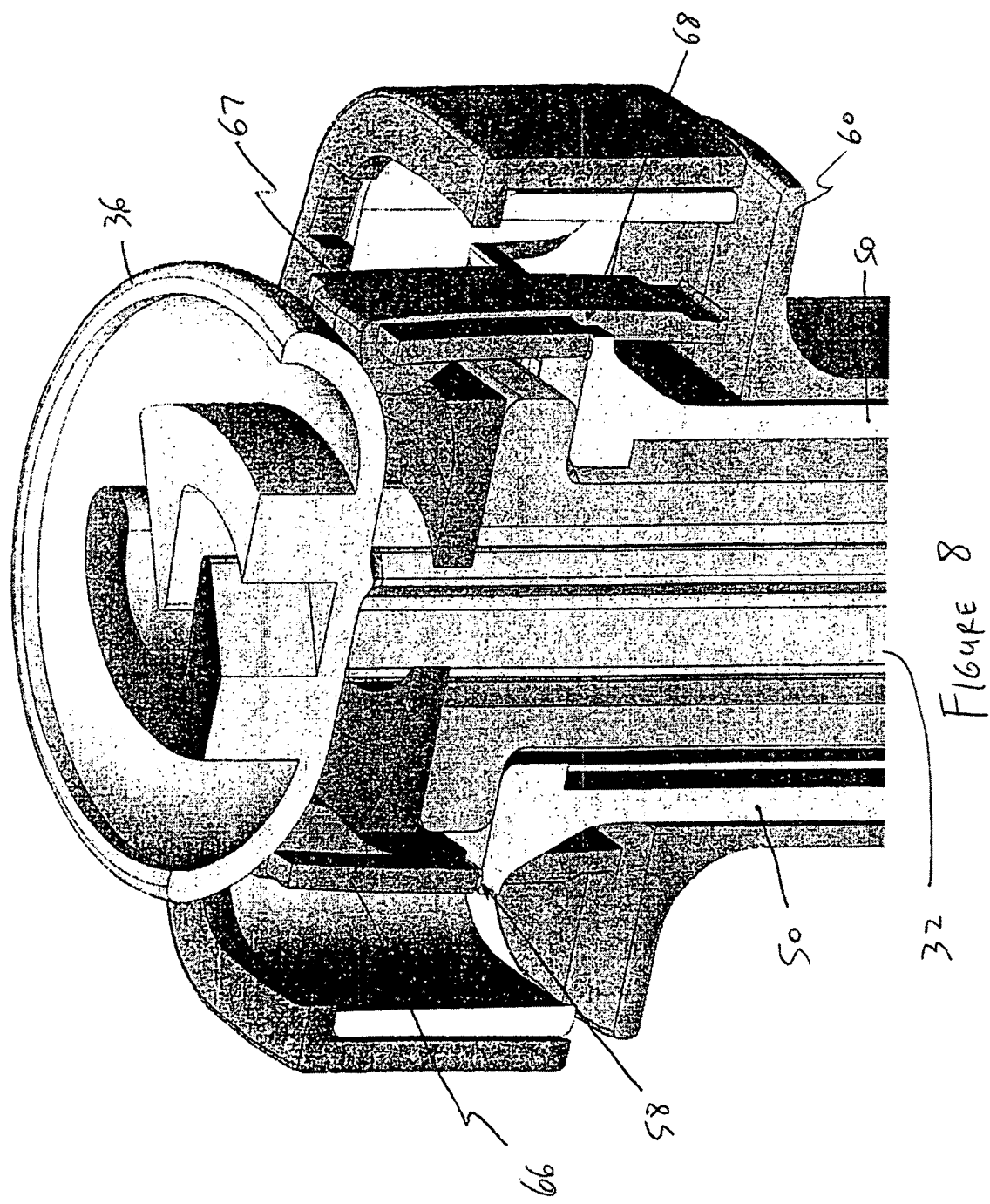
FIG. 8 shows a cut away view of the diagram in FIG. 7. The shield trigger fingers are shown engaging the body in the latched position. The latched position is achieved by contact between the latch surfaces of the shield trigger fingers and the body.

The shield 60 is a tubular member adapted to slidably fit on the body 50 and has a proximal end 62 and a distal end 64. In a preferred embodiment, one or more trigger fingers 66 extend proximally from the proximal end 62 of the shield 60 (FIGS. 7-9). The trigger fingers 66 may include a first catch 68 that is configured to engage a second catch 58 on the proximal end 52 of the body 50 of the needle guard 40 (FIGS. 8 and 9). Engagement between the first catch 68 and the second catch 58 retains the shield 60 in a first, retracted position. This latched configuration is further secured by an angled orientation of the latch surfaces, which when combined with the force of the spring 55 urging these surfaces against each other, places a component of force on the trigger fingers 66 directed toward the centerline. Preferably, the one or more trigger fingers 66 are elongate fingers having a proximal tip 67 that is engageable by the thumb pad 36 of the plunger 30 as it is depressed to axially compress and deflect the one or more trigger fingers 66 radially outwardly, as is discussed further below.

The passive needle guard 40 also preferably includes a spring mechanism 55 coupled to the body 50 and the shield 60 for biasing the shield 60 towards an extended position when the trigger fingers 66 are deflected radially (FIG. 10).

The back plate 90 is removably coupled with the needle guard 40. The back plate 90 creates a physical barrier to removal of the plunger from the needle guard safety device 5. The back plate 90 includes an aperture 92 dimensioned to receive the stem 32 of the plunger 30, wherein the aperture is of a smaller size than a distal end of the plunger. When the plunger is moved proximally, the back plate 90 prevents a user from accidentally removing the plunger 30.

The syringe 10 can be used to administer a lyophilized or concentrated drug to a patient. The lyophilized drug or concentrated drug may be of any type known to those of skill in the art. Preferably, the lyophilized or concentrated drug is stored in a vial 200 or container such as a glass vial (FIG. 1). The vial 200 may include a cover 210 such as a rubber stopper, septum, or cap that can be penetrated by a needle. In a preferred embodiment, the vial 200 is made of a substantially clear glass so that the user can ensure that the diluent and lyophilized drug have been properly and fully mixed.

Figure 3:
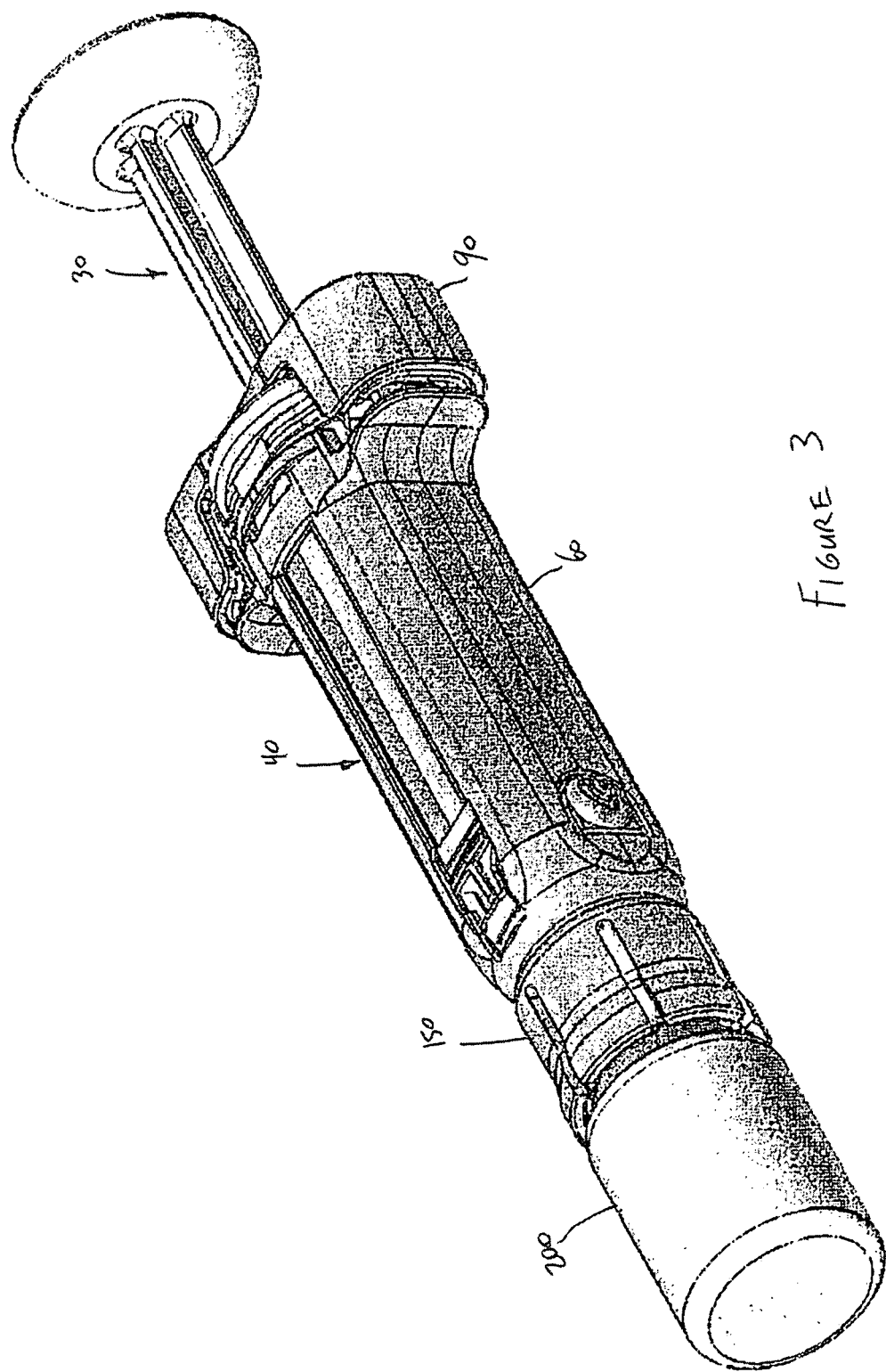
FIG. 3 shows an exemplary embodiment of the device wherein a drug vial is removably coupled with the drug vial adaptor.

The drug vial adaptor 150 connects onto the end of the vial 200 that has the septum (FIGS. 1 and 3-5). The vial adaptor 150 has a thin pointed distal end 152 and a luer fitting 154 on the proximal end 156. An inner channel runs from the sharp distal end 152 to the proximal luer fitting 154 (FIG. 2). The vial adaptor luer fitting 154 is attached to the luer fitting 17 on the syringe 10 and the vial adaptor 150 is then attached to the vial 200 (FIGS. 2 and 3). The sharp distal end 152 of the vial adaptor 150 is sized to penetrate the vial septum as it connects to the vial 200, thus creating a fluid channel between the syringe 10 and vial 200.

Figure 4:
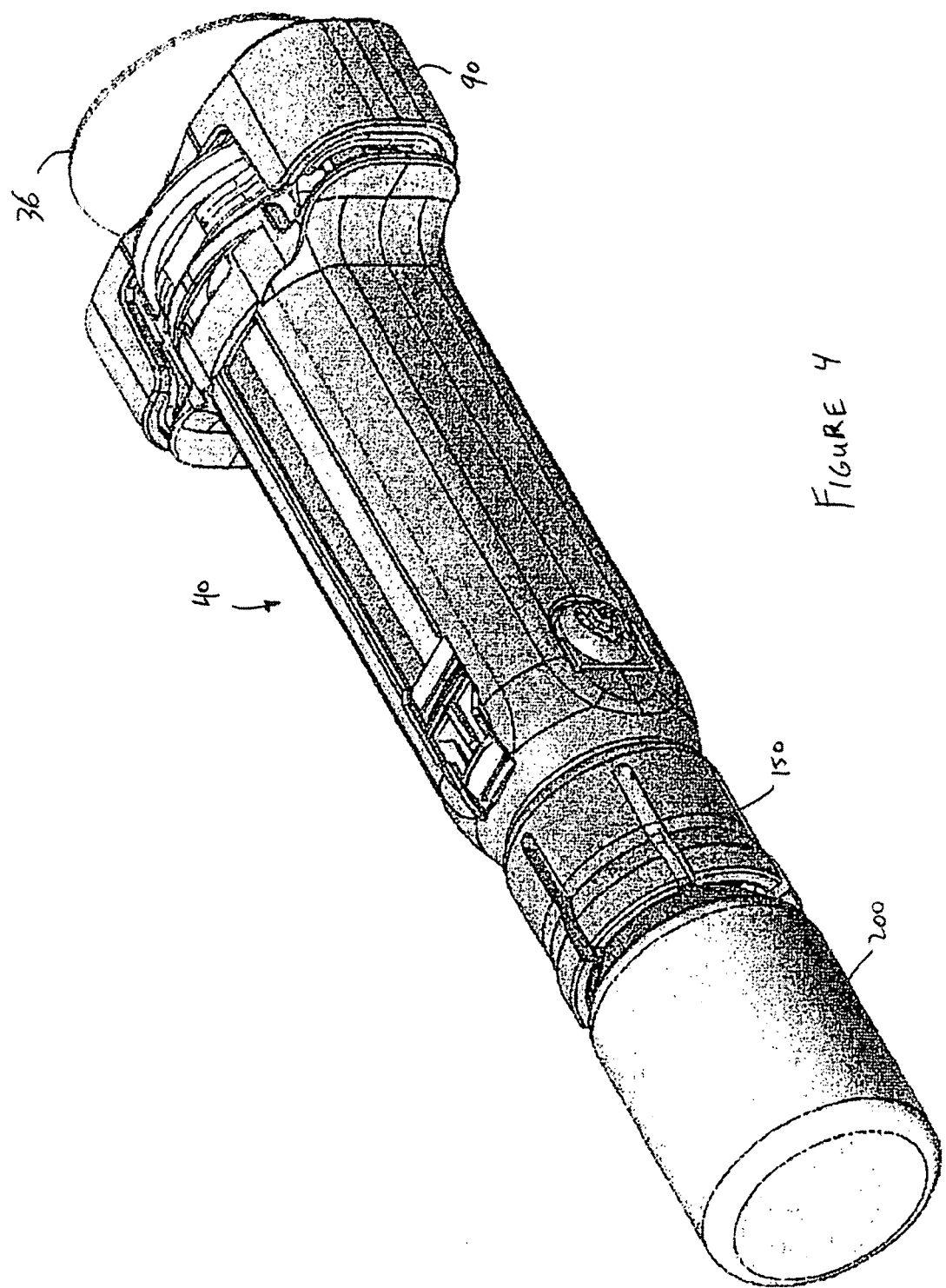
FIG. 4 shows an exemplary embodiment of the device with the plunger pushed distally to expel the diluent in the syringe into the vial for the purpose of reconstituting the drug in the vial.

The steps of reconstituting the drug and administering it into the patient would be to install the drug vial adaptor 150 onto the syringe 10 inside the needle guard 40 via their respective luer fittings 17, 154 (FIG. 2). The drug vial 200 is then attached to the drug vial adaptor 150 creating a fluid-communicating channel between the vial 200 and the syringe 10 (FIG. 3). The plunger 30 is then advanced to expel the diluent from the syringe 10 into the drug vial 200 (FIG. 4).

It is at this point that the problems with existing safety devices would arise, since advancing the plunger 30 to expel the diluent in the drug vial 200 would trigger the safety shield mechanism of exiting safety devices. With the shield now covering the distal end of the device, the rest of the reconstitution steps would be impossible to perform and, additionally, the injection needle would not be accessible in order to inject the patient.

To prevent the relative motion of the safety shield 60 during the steps of reconstitution, it has been discovered that a component (e.g., a vial adaptor 150) attached to the luer connection 17 of the syringe 10 will prevent the relative motion of the safety shield 60 if it is of a sufficient diameter and proximity to the safety shield 60. As the vial adaptor 150 is installed and tightened onto the syringe luer fitting 17, it will be advanced proximally relative to the safety shield 60, and when appropriately sized, will come in proximity to the safety shield 60 in a manner preventing any distal motion of the safety shield 60 relative to the syringe 10 or the rest of the safety device 5.

The plunger 30 can then travel the full stroke to empty the syringe contents during reconstitution. Even though the safety shield mechanism will have been triggered (i.e. the thumb pad 36 will contact the trigger fingers 66), the shield 60 will not advance to the shielded position because the interaction of the vial adaptor 150 (or other component), shield 60, and luer fitting 17 prevents it from doing so. Because the trigger fingers 66 have an elastic force urging them back into the latched position, the latch mechanism is reversible if the shield 60 has not moved forward. When the plunger 30 is pulled proximally to draw the drug mixture from the vial 200 into the syringe 10, the trigger fingers 66 will relatch themselves against the second catch 58 on the body 50 so that the needle guard 40 is able to trigger the next time the plunger 30 is advanced sufficiently distally.

Figure 5:
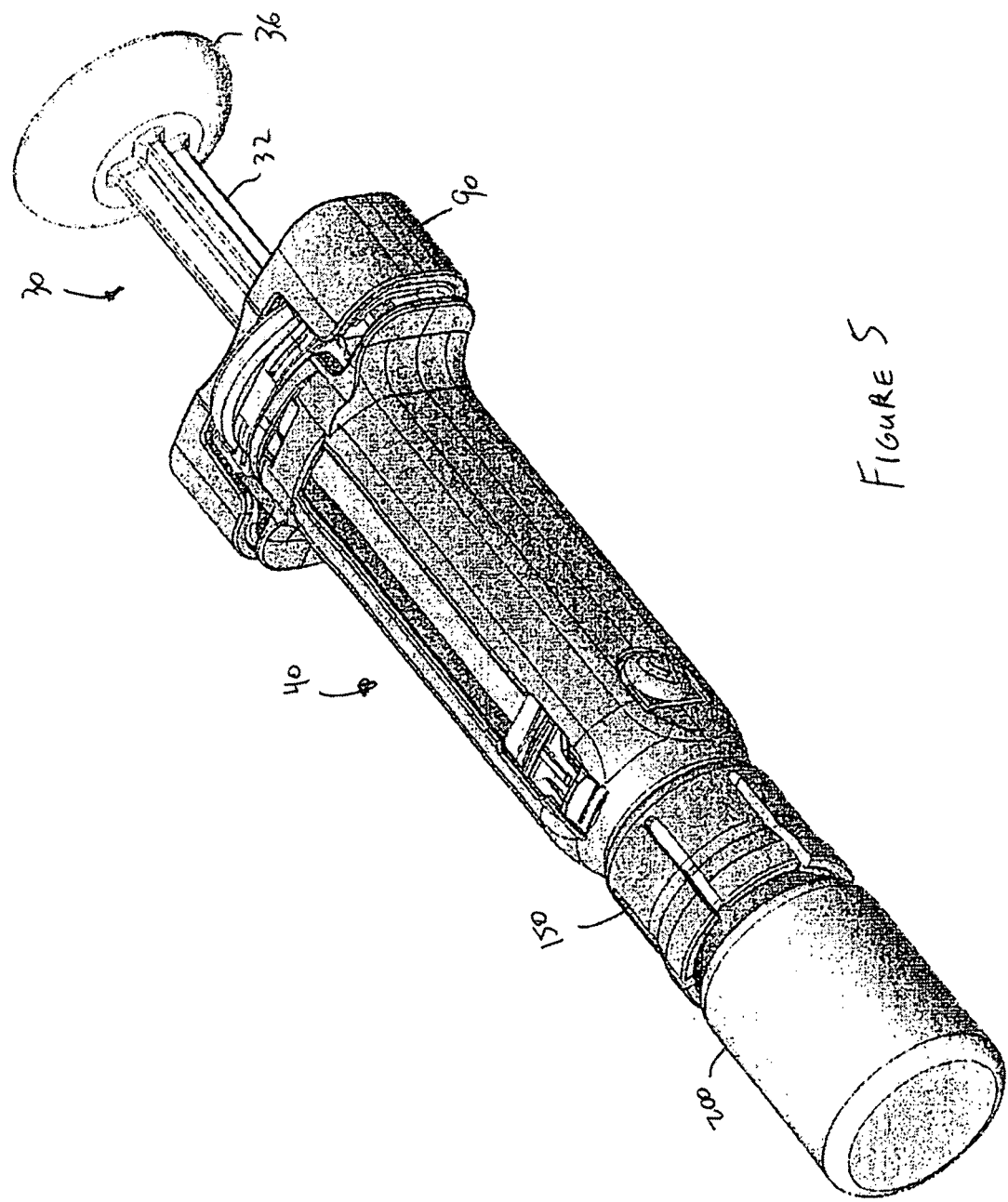
FIG. 5 shows exemplary embodiment of the device with the plunger pulled back proximally after the drug has been reconstituted in the step depicted in FIG. 4.

After the drug has been dissolved in the diluent, the plunger 30 is withdrawn proximally, pulling the drug mixture into the syringe 10 (FIG. 5). In a preferred embodiment, a circumferential rib 35 on the distal end 34 of the plunger 30 interferes with the plunger support back plate 90 preventing the full withdrawal of the plunger 30, so that users will not inadvertently and surprisingly remove the stopper 20 from the syringe 10 and expose the drug to a non-sterile environment (FIG. 1). The vial adaptor 150 (with the vial 200) is removed from the syringe luer fitting 17 and replaced with an injection needle 15 having a luer fitting (FIG. 6). The medication is now ready for injection into the patient and the needle guard 40 should deploy in the normal manner after the medication has been injected into the patient.

As discussed above, the thumb pad 36 of the plunger 30 is sized and shaped to displace the trigger fingers 66 laterally away from the latched position that connects them to the body 50 to an unlatched position that substantially disconnects them from the body 50 when the plunger is advanced sufficiently far forward distally, preferably far enough forward that the contents of the syringe 10 has been expelled, but before the plunger 30 is arrested by the stopper 20 reaching the distal end of the syringe 10 (FIG. 9). As the medication is being injected into the patient with the vial adaptor 150 removed, the plunger 30 will displace the trigger fingers 66 causing the force of the spring 55 to move the shield 60 forward preventing the trigger fingers 66 from relatching and initiating the deployment of the safety shield 60. The dotted lines in FIG. 9 depict the movement of the trigger fingers 66 from the latched position to the unlatched position.

After the plunger 30 is fully advanced and the safety shield mechanism has been released, the shield 60 is either moved distally relative to the syringe 10 and needle 15 or the syringe 10 and needle 15 are moved proximally with respect to the shield 60. Passive or automatic deployment of the safety shield 60 is accomplished by way of the compression spring 55 pushing the shield 60 distally and/or the syringe 10 and needle 15 proximally. The spring force is released to the shield 60 and body 50 when the trigger fingers 66 are displaced from the latch configuration. The spring 55 is of sufficient size to move the shield 60 far enough to sufficiently shield the needle 15 from the user (FIG. 10). In a preferred embodiment, a locking mechanism holds the shield in the extended position. The locking mechanism may comprise, for example, a set of cooperating detents or catches on the shield 60 and body 50 that maintain the shield in the extended position. Regardless of the relative motion of the safety shield 60, what is common to all devices is that the safety shield 60 is actuated after the plunger has been advanced to empty the syringe contents.

Examples of devices that could be used to attach to the syringe luer fitting and to prevent the forward advance of the shield are not limited to drug vial luer adaptors 150. Others could include female-to-female and female-to-male luer adaptors, luer adaptor fittings on disposable sets, filters with luer fittings, etc. provided that they have the correct geometry to prevent the shield from deploying. In addition, luer connections are widely used in the medical device industry, but any similar releasable connection could also function to hold the drug vial or similar device in proximity to the shield to prevent it from being deployed.

Although preventing the shield from deploying or moving distally over the syringe has been described, it is understood that the present invention would also apply to devices that move the syringe and needle proximally. Furthermore, the trigger finger based latch mechanism has been described in detail, but it is understood that any mechanism that triggers the deployment of a safety shield could be used.

While the invention is susceptible to various modifications, and alternative forms, specific examples thereof have been shown in the drawings and herein described in detail. It should be understood, however, that the invention is not to be limited to the particular forms or methods disclosed, but to the contrary, the intention is to cover all modifications, equivalents, and alternatives falling within the spirit and scope of the appended claims.

What is claimed:

1. A syringe system for administering lyophilized drugs, the syringe system comprising a needle guard, the needle guard comprising a shield;

a body;

one or more trigger fingers disposed on a proximal region of the body or shield;

one or more catches disposed on the body or shield, wherein the catches are configured to retain the trigger fingers in a resting, latched position and the shield in a first, retracted position until the trigger fingers are unlatched; and a spring, wherein the spring is configured to bias the shield to move from the first, retracted position to a second, extended position if the trigger fingers are unlatched;

a syringe removably coupled with the body of the needle guard, the syringe including a cylindrical barrel, a port extending from the distal, administration end of the barrel, and a plunger slidably coupled with the cylindrical barrel, wherein the port is positioned adjacent the distal end of the shield and a needle is couplable to the port and extendible beyond the shield when the shield is in the first, retracted position, wherein the plunger comprises a stem and a thumb pad on the proximal end of the stem, wherein the stem and thumb pad are configured to enable the thumb pad to contact and unlatch the trigger fingers when the plunger is advanced to a distal position within the barrel of the syringe during reconstitution of a drug within the syringe and injection of a drug within the syringe into a patient; and a component removably coupled to the port of the syringe and configured to retain the shield in the first, retracted position when the trigger fingers are unlatched as the thumb pad moves distally and contacts the trigger fingers as the plunger is advanced to a distal position within the barrel of the syringe during reconstitution of a drug within the syringe, wherein the component is dimensioned to abut the distal end of the shield, and wherein the trigger fingers are relatchable to the resting, latched position to retain the shield in a first, retracted position when the thumb pad moves out of contact with the trigger fingers as the plunger is withdrawn proximally during reconstitution of a drug within the syringe, and wherein the trigger fingers are biased to relatch to the resting position when the component is attached to the port and the thumb pad is withdrawn proximally to disengage from contact with the trigger fingers.

2. The system of claim 1, wherein the cylindrical barrel is filled with a diluent.

3. The syringe system of claim 2, wherein the diluent comprises sterile water.

4. The syringe system of claim 2, wherein the diluent comprises saline.

5. The syringe system of claim 1, wherein the port comprises a luer port.

6. The syringe system of claim 1, wherein the component comprises a luer connector.

7. The syringe system of claim 1, wherein the component comprises a vial adaptor.

8. The syringe system of claim 1, wherein the port is configured to receive a needle.

9. The syringe system of claim 7, wherein the vial adaptor comprises a sharp distal end.

10. The syringe system of claim 7, wherein the proximal end of the vial adaptor comprises a luer fitting.

11. The syringe system of claim 7, wherein the vial adaptor comprises panels configured to receive a vial bottle.

12. A syringe system for administering lyophilized drugs, the syringe system comprising a needle guard, the needle guard comprising
a shield;
a body;
one or more trigger fingers disposed on a proximal region of the body or shield;
one or more catches disposed on the body or shield, wherein the catches are configured to retain the trigger fingers in a resting, latched position and the shield in a first, retracted position until the trigger fingers are unlatched; and
a spring, wherein the spring is configured to bias the shield to move from the first, retracted position to a second, extended position if the trigger fingers are;

a syringe removably coupled with the body of the needle guard, the syringe including a cylindrical barrel, a port extending from the distal, administration end of the barrel, and a plunger slidably coupled with the cylindrical barrel wherein the port is positioned adjacent the distal end of the shield and a needle is couplable to the port and extendible beyond the shield when the shield is in the first, retracted position, wherein the plunger comprises a stem and a thumb pad on the proximal end of the stem, wherein the stem and thumb pad are configured to enable the thumb pad to contact and unlatch the trigger fingers when the plunger is advanced to a distal position within the barrel of the syringe during reconstitution of a drug within the syringe and injection of a drug within the syringe into a patient, a component removably coupled to the port of the syringe and configured to retain the shield in the first, retracted position when the trigger fingers are unlatched as the thumb pad moves distally and contacts the trigger fingers as the plunger is advanced to a distal position within the barrel of the syringe during reconstitution of a drug within the syringe, wherein the component is dimensioned to abut the distal end of the shield, wherein the trigger fingers are relatchable to the resting, latched position to retain the shield in a first, retracted position when the thumb pad moves out of contact with the trigger fingers as the plunger is withdrawn proximally during reconstitution of a drug within the syringe, and wherein the trigger fingers are biased to relatch to the resting position when the component is attached to the port and the thumb pad is withdrawn proximally to disengage from contact with the trigger fingers; and a back plate removably coupled with the proximal portion of the needle guard, the back plate including an aperture configured to receive the stem of the plunger and to prevent removal of the plunger from the barrel.

13. The syringe system of claim 12, wherein the port comprises a luer port.

14. The syringe system of claim 12, wherein the component comprises a luer connector.

15. The syringe system of claim 12, wherein the component comprises a vial adaptor.

16. The syringe system of claim 12, wherein the port is configured to receive a needle.

* * * * *